US010927101B2

(12) United States Patent
Han et al.

(10) Patent No.: US 10,927,101 B2
(45) Date of Patent: Feb. 23, 2021

(54) NEOPETROSIDES A AND B, AND SYNTHESIS METHOD THEREOF

(71) Applicant: INJE UNIVERSITY INDUSTRY-ACADEMIC COOPERATION FOUNDATION, Gimhae-si (KR)

(72) Inventors: Jin Han, Busan (KR); Seung Hun Jeong, Busan (KR); In-Sung Song, Yangsan-si (KR); Hyoung Kyu Kim, Busan (KR); Nari Kim, Busan (KR); Larisa K. Shubina, Vladivostok (RU); Tatyana N. Makarieva, Vladivostok (RU); Valentin A. Stonik, Vladivostok (RU); Dmitry V. Yashunsky, Moscow (RU); Nikolay E. Nifantiev, Moscow (RU)

(73) Assignee: INJE UNIVERSITY INDUSTRY-ACADEMIC COOPERATION FOUNDATION, Gimhae-si (KR)

( * ) Notice: Subject to any disclaimer, the term of this patent is extended or adjusted under 35 U.S.C. 154(b) by 0 days.

(21) Appl. No.: 16/327,330

(22) PCT Filed: May 30, 2017

(86) PCT No.: PCT/KR2017/005645
§ 371 (c)(1),
(2) Date: Feb. 22, 2019

(87) PCT Pub. No.: WO2017/209494
PCT Pub. Date: Dec. 7, 2017

(65) Prior Publication Data
US 2019/0218206 A1    Jul. 18, 2019

(30) Foreign Application Priority Data
May 31, 2016    (KR) .................. 10-2016-0067450

(51) Int. Cl.
| C07D 405/04 | (2006.01) |
| C07D 405/14 | (2006.01) |
| A23L 33/10 | (2016.01) |
| A61K 31/443 | (2006.01) |
| A61P 9/10 | (2006.01) |
| A61P 9/04 | (2006.01) |
| A61P 9/14 | (2006.01) |

(52) U.S. Cl.
CPC ............ *C07D 405/04* (2013.01); *A23L 33/10* (2016.08); *A61K 31/443* (2013.01); *A61P 9/04* (2018.01); *A61P 9/10* (2018.01); *A61P 9/14* (2018.01); *C07D 405/14* (2013.01)

(58) Field of Classification Search
CPC .................................................. C07D 405/04
See application file for complete search history.

(56) References Cited

PUBLICATIONS

Shubina, L.K., et al. "Pyridine Nucleosides Neopetrosides A and B from a Marine *Neopetrosia* sp. Sponge. Synthesis of Neopetroside A and Its β-Riboside Analogue." J. Natural Products. (2015), vol. 78, No. 6, pp. 1383-1389. (Year: 2015).*
International Search Report for PCT/KR2017/005645 dated Aug. 30, 2017 from Korean Intellectual Property Office.
Franchetti, P. et al., "Stereoselective Synthesis of Nicotinamide β-Riboside and Nucleoside Analogues", Bioorganic & Medicinal Chemistry Letters, 2004, vol. 14, No. 18, pp. 4655-4658.
Friedlos, F et al., "Identification of novel reduced pyridinium derivatives as synthetic co-factors for the enzyme DT diaphorase (NAD(P)H dehydrogenase (quinone), EC 1.6.99.2)", Biochemical Pharmacology, 1992, vol. 44, No. 1, pp. 25-31.
Davies, L. C. et al., "Simple Synthesis of the 5-O-Benzoylriboside of 1,4-Dihydronicotinic Acid; a Cofactor for DT Diaphorase and Nitroreductase Enzymes", Nucleosides & Nucleotides, 1995, vol. 14, Nos. 3-5, pp. 311-312.
Shubina, L. K. et al., "Pyridine Nucleosides Neopetrosides A and B from a Marine *Neopetrosia* sp. Sponge. Synthesis of Neopetroside A and Its β-Riboside Analogue", Journal of Natural Products, Jun. 2, 2015, vol. 78, No. 6, pp. 1383-1389.
Gribble, G. W. et al., "Six-Membered Ring Systems: Pyridine and Benzo Derivatives", Progress in Heterocyclic Chemistry, 1st Edition. Elsevier LTD. Sep. 23, 2016, vol. 28, total pp. 682.

* cited by examiner

*Primary Examiner* — John S Kenyon
(74) *Attorney, Agent, or Firm* — Revolution IP, PLLC (57) ABSTRACT

The present invention relates to novel pyridine nucleoside compounds, Neopetroside A (NPS A) and Neopetroside B (NPS B) obtained by fractionating an extract of *Neopetrosia* sp. which is a marine sponge, with ethanol, into n-butanol (n-BuOH). When the NPS A was treated with myocardial cells, it activates oxidative phosphorylation, basal and mitochondrial respiration induced by ATP and ATP synthesis, and stimulates the glycolysis activity and when the NPS A was treated with an ischemic reperfusion injury model, the left ventricular pressure injured by ischemic reperfusion was recovered and the size of myocardial injury site was significantly reduced and as a result, can be provided as the pharmaceutical composition for preventing or treating ischemic heart disease or the health functional food for preventing or improving the same.

4 Claims, 6 Drawing Sheets

NEOPETROSIDES A AND B, AND SYNTHESIS METHOD THEREOF

CROSS REFERENCE TO PRIOR APPLICATIONS

This application is the 35 U.S.C. 371 national stage of International application PCT/KR2017/005645 filed on May 30, 2017; which claims priority to Korean application 10-2016-0067450 filed on May 31, 2016. The entire contents of each of the above-identified applications are hereby incorporated by reference.

TECHNICAL FIELD

The present invention relates to a novel pyridine nucleoside compound extracted from *Neopetrosia* sp. which is a marine sponge, and medical use thereof.

BACKGROUND ART

Ischemic heart diseases such as myocardial infarction, arrhythmia and heart failure, etc. caused by myocardial cell damage and cardiac function during ischemic reperfusion are high in prevalence and mortality and difficult to cure completely, and intensive basic and clinical studies have been conducted over the past 50 years.

Because ischemic reperfusion injury is involved in various physiological mechanisms such as metabolism, immune response, changes in ion homeostasis, oxygen free radicals, etc., studies have been conducted in various fields such as immunomodulators, apoptosis-related substances, and ion channel regulators. The development of therapeutic agents and surgical treatments with new points of action have been actively carried out together with the study of the mechanism, but the technology to protect the myocardial cells from ischemic reperfusion has not yet commercialized clinically.

It is known that reperfusion injury such as myocardial infarction recurrence, cardiac dysfunction, arrhythmia, and neuropsychiatric depression shows at a high rate, even after surgical operation such as coronary artery bypass surgery, coronary angioplasty, and reperfusion therapy by drug therapy such as thrombolysis.

Therefore, in the treatment of ischemic heart disease, it requires to develop a substance capable of slowing the progression of myocardial cell damage and alleviating reperfusion injury.

DISCLOSURE

Technical Problem

Accordingly, it is an object of the present invention to provide a novel compound having an effect of treating ischemic heart disease.

Also, it is another object of the present invention to provide a method of preparing a novel compound having an effect of treating ischemic heart disease.

In addition, it is another object of the present invention to provide a pharmaceutical composition for preventing or treating ischemic heart disease.

Furthermore, it is another object of the present invention to provide a health functional food for preventing or improving ischemic heart disease.

Technical Solution

In order to accomplish the above object, the present invention provides a pyridine nucleoside compound represented by the following Chemical Formula 1 or a pharmaceutically acceptable salt thereof:

[Chemical Formula 1]

in Chemical Formula 1, $R^1$ is a heteroaromatic group or phenol.

The pyridine nucleoside compound may be a compound represented by the following Chemical Formula 2 or Chemical Formula 3.

[Chemical Formula 2]

[Chemical Formula 3]

Also, the present invention provides a method for synthesizing a pyridine nucleoside compound represented by Chemical Formula 2 or a pharmaceutically acceptable salt thereof.

To accomplish another object, the present invention provides a pharmaceutical composition for preventing or treating ischemic heart disease comprising a pyridine nucleoside compound represented by the Chemical Formula 1 or a pharmaceutically acceptable salt thereof, as an active ingredient.

To accomplish another object, the present invention provides a health functional food for preventing or improving ischemic heart disease comprising a pyridine nucleoside compound represented by the Chemical Formula 1 or a pharmaceutically acceptable salt thereof, as an active ingredient.

Advantageous Effects

The present invention relates to novel pyridine nucleoside compounds, Neopetroside A (NPS A) and Neopetroside B (NPS B) which are obtained by fractionating an extract which a marine sponge, *Neopetrosia* sp. is extracted with ethanol, using n-butanol (n-BuOH). When the NPS A was treated with myocardial cells, oxidative phosphorylation, basal and mitochondrial oxygen consumption rate, and ATP-related breathing and ATP synthesis were activated, and the glycolysis is stimulated, and when the NPS A was treated with an ischemic reperfusion injury model, the pressure of left ventricle injured by ischemic reperfusion was restored and the size of the myocardial injury area was significantly reduced.

DESCRIPTION OF DRAWINGS

FIG. 6A and FIG. 6B show the results of the left ventricular pressure (LV pressure) of the positive control group, and the LV pressure of the test group treated with NPS A, respectively.

BEST MODE

Hereinafter, the present invention will be described in detail.

Figure 1:
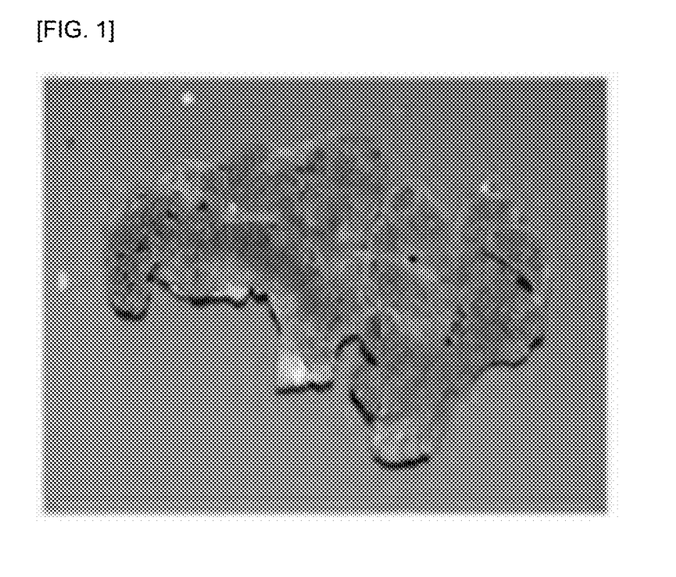
FIG. 1 is an image of *Neopetrosia* sp., a marine sponge.

The inventors of the present invention extracted a novel pyridine nucleoside compound from *Neopetrosia* sp., a marine sponge of FIG. 1 and confirmed the therapeutic effect of the compound for ischemic heart disease, and thus completed the present invention.

The *Neopetrosia* sp. sponge was cultivated in May 2010 at Con Son Island (Vietnam, 08° 40'N; 106° 44'4 E, depth 6-15 m) through a scuba during a 38th systematic cruise by R/V Academic Oparin of Pacific Institute of Bioorganic Chemistry (PIBOC) in Russia.

*Neopetrosia* sp. marine sponge has thickness of 1-2 cm and various shapes and the surface thereof is generally uniform and has a soft or slightly velvety touch. The oscule is sporadically present at intervals of up to 5 mm in diameter, the exterior color is dull blue, the interior color is cream, and the solid, fragile, dense and choanosomal skeleton.

Accordingly, the present invention provides a pyridine nucleoside compound represented by the following Chemical Formula 1 or a pharmaceutically acceptable salt thereof:

[Chemical Formula 1]

in Chemical Formula 1, $R^1$ is a heteroaromatic group or phenol.

The pyridine nucleoside compound is preferably a compound represented by the following Chemical Formulae 2 or 3, wherein the compound represented by Chemical Formula 2 is Neoperoside A (NPS A), and the compound represented by Chemical Formula 3 is Neoperoside B (NPS B).

[Chemical Formula 2]

[Chemical Formula 3]

The pyridine nucleoside compound may be extracted from *Neopetrosia* sp. marine sponge, and more specifically, the *Neopetrosia* sp. marine sponge is obtained by extracting *Neopetrosia* sp. marine sponge with a solvent selected from the group consisting of water, C1-C4 alcohol and a mixture thereof and fractionating with C1-C4 alcohol.

In addition, the NPS A can also be obtained through the synthesis as shown in Reaction Scheme 1 below.

[Reaction Scheme 1]

Accordingly, the present invention provides a method of preparing a pyridine nucleoside compound represented by Chemical Formula 2 or a pharmaceutically acceptable salt thereof, as Reaction Scheme 1, comprising: preparing riboside compound of Compound 10 by adding acetoxybenzoyl chloride to riboside solution of Compound 9; preparing a nicotinoyl riboside compound of Compound 11 by adding ethyl nicotinate to the riboside solution of Compound 10; preparing a nicotinoyl riboside compound of Compound 12 by adding an ammonium solution to the nicotinoyl ribose solution of Compound 11; and preparing a neopetroside compound of Compound 8 by dissolving nicotinoyl ribose of the Compound 12 in an aqueous solution of trifluoroacetic acid, and concentrating and lyophilizing.

In addition, according to the present invention, when the NPS A was treated with myocardial cells, oxidative phosphorylation, basal and mitochondrial oxygen consumption rate, and ATP-related breathing and ATP synthesis were activated, and the glycolysis is stimulated, and when the NPS A was treated with an ischemic reperfusion injury model, the pressure of left ventricle injured by ischemic reperfusion was restored and the size of the myocardial injury area was significantly reduced.

Accordingly, the present invention can provide a pharmaceutical composition for preventing or treating ischemic heart disease comprising a pyridine nucleoside compound represented by the following Chemical Formula 1 or a pharmaceutically acceptable salt thereof, as an active ingredient:

[Chemical Formula 1]

in Chemical Formula 1, $R^1$ is a heteroaromatic group or phenol.

The pyridine nucleoside compound is preferably a compound represented by the following Chemical Formula 2 or 3, wherein the compound represented by Chemical Formula

2 is Neoperoside A (NPS A), the compound represented by Chemical Formula 3 is a neo And Neoperoside B (NPS B).

The pyridine nucleoside compound is preferably a compound represented by the following Chemical Formulae 2 or 3, wherein the compound represented by Chemical Formula 2 is Neoperoside A (NPS A), and the compound represented by Chemical Formula 3 is Neoperoside B (NPS B).

[Chemical Formula 2]

[Chemical Formula 3]

The ischemic heart disease may be selected from the group consisting of myocardial infarction, heart failure and angina pectoris, more preferably myocardial infarction.

The pharmaceutical composition may contain 0.01 to 90 parts by weight of a pyridine nucleoside compound based on 100 parts by weight of the total pharmaceutical composition.

The pharmaceutical composition for preventing or treating ischemic heart disease according to the present invention may be used as any one formulation selected from the group consisting of an injection, a granule, a powder, a tablet, a pill, a capsule, a suppository, a gel, a suspension, an emulsion, a drop, and liquid, according to a conventional method.

Specific examples of carriers, excipients and diluents include lactose, dextrose, sucrose, sorbitol, mannitol, xylitol, erythritol, maltitol, starch, acacia rubber, alginate, gelatin, calcium phosphate, calcium silicate, cellulose, methylcellulose, microcrystalline cellulose, polyvinylpyrrolidone, water, methylhydroxybenzoate, propylhydroxybenzoate, talc, magnesium stearate and mineral oil. Solid formulations for oral administration may include tablets, pills, powders, granules, capsules, etc. and these solid formulations can be prepared by mixing at least one excipient such as starch, calcium carbonate, sucrose or lactose, gelatin and the like in the composition. In addition to simple excipients, lubricants such as magnesium stearate and talc may also be used. Examples of the liquid formulation for oral administration include suspensions, solutions, emulsions or syrups, etc. and various excipients such as wetting agents, sweeteners, fragrances, preservatives, etc. in addition to water and liquid paraffin, which are commonly used simple diluents. Formulations for parenteral administration include sterilized aqueous solutions, non-aqueous solutions, suspensions, emulsions, freeze-dried preparations, suppositories, and the like.

Examples of the non-aqueous solutions or suspensions include propylene glycol, polyethylene glycol, vegetable oil such as olive oil, injectable ester such as ethyl oleate, and the like. As the suppository base, witepsol, macrogol, tween 61, cacao paper, laurin, glycerogelatin and the like can be used.

According to one embodiment of the present invention, the pharmaceutical composition may be administered to a subject in a conventional manner via intravenous, intraarterial, intraperitoneal, intramuscular, intrasternal, transdermal, nasal, inhaled, topical, rectal, oral, intraocular or intradermal routes.

The preferred dosage of the pyridine nucleoside compound may vary depending on the condition and body weight of the subject, the type and degree of disease, the drug form, the administration route and the period, and may be appropriately selected by those skilled in the art. According to one embodiment of the present invention, the daily dosage may be 0.01 to 200 mg/kg, specifically 0.1 to 200 mg/kg, more specifically 0.1 to 100 mg/kg, though it is not limited thereto. The administration may be carried out once a day or divided into several times, so that the scope of the present invention is not limited thereto.

In the present invention, the 'subject' may be a mammal including a human, but it is not limited thereto.

In addition, the present invention can provide a health functional food for preventing or improving ischemic heart disease comprising a pyridine nucleoside compound represented by the following Chemical Formula 1 or a pharmaceutically acceptable salt thereof, as an active ingredient:

[Chemical Formula 1]

in Chemical Formula 1, $R^1$ is a heteroaromatic group or phenol.

The pyridine nucleoside compound is preferably a compound represented by the following Chemical Formulae 2 or 3, wherein the compound represented by Chemical Formula 2 is Neoperoside A (NPS A), and the compound represented by Chemical Formula 3 is Neoperoside B (NPS B).

[Chemical Formula 2]

-continued

[Chemical Formula 3]

The ischemic heart disease may be selected from the group consisting of myocardial infarction, heart failure and angina pectoris, more preferably myocardial infarction.

The health functional food is used together with other food or food additives other than the pyridine nucleoside compound, and can be suitably used according to a conventional method. The amount of the active ingredient to be mixed can be appropriately determined according to its use purpose, for example, prevention, health or therapeutic treatment.

The effective dose of the compound contained in the health functional food may be used in accordance with the effective dose of the therapeutic agent. However, in the case of long-term intake for the health and hygiene or for health control purposes, it may be used in the above range or lower, and it is clear that the active ingredient can be used in an amount of at least the above range because there is no problem in terms of safety.

There is no particular limitation regarding the kind of the health functional food. Examples of the health functional food include meat, sausage, bread, chocolate, candy, snack, confectionery, pizza, ramen, other noodles, gums, dairy products including ice cream, various soups, beverages, tea, drinks, alcoholic beverages and vitamins complex, etc.

The pyridine nucleoside compound represented by Chemical Formula 1 of the present invention can be used in the form of a pharmaceutically acceptable salt, and the salt can be used in any form of a pharmaceutically acceptable basic salt or acidic salt. The basic salt can be used in the form of an organic base salt or an inorganic base salt and can be selected from the group consisting of a sodium salt, a potassium salt, a calcium salt, a lithium salt, a magnesium salt, a cesium salt, an aminium salt, an ammonium salt and a pyridinium salt, but it is not limited thereto.

Also, acid salt is useful as acid addition salt formed by free acids. As the free acid, inorganic acid and organic acid can be used. As the inorganic acid, hydrochloric acid, bromic acid, sulfuric acid, sulfurous acid, phosphoric acid and the like can be used, and as the organic acid, citric acid, acetic acid, maleic acid, fumaric acid, glucosan, benzenesulfonic acid, camphorsulfonic acid, oxalic acid, malonic acid, glutaric acid, acetic acid, glyconic acid, succinic acid, tartaric acid, 4-toluenesulfonic acid, galacturonic acid, embonic acid, glutamic acid, citric acid, aspartic acid, and the like can be used. Preferably, hydrochloric acid is used as the inorganic acid, and methanesulfonic acid is used as the organic acid.

In addition, the pyridine nucleoside compound represented by Chemical Formula 1 of the present invention includes not only pharmaceutically acceptable salts, but also all salts, hydrates and solvates which can be prepared by the conventional methods.

The addition salt according to the present invention can be prepared by the conventional methods, for example, by dissolving the pyridine nucleoside compound represented by the Chemical Formula 1 in a water-miscible organic solvent such as acetone, methanol, ethanol, or acetonitrile, and adding an excess organic base or by adding an aqueous base solution of an inorganic base and precipitating or crystallizing the base. Or it can be prepared by evaporating a solvent or excess base from the mixture and then drying it to obtain an additional salt or by subjecting the precipitated salt to suction filtration.

Hereinafter, the present invention will be described in detail with reference to the following examples. It should be noted, however, that the following examples are illustrative of the present invention and are not intended to limit the scope of the present invention. The examples of the present invention are provided to more fully describe the present invention to those skilled in the art.

<Example 1> Extraction and Synthesis of Neopetroside A (NPS A)

1. Extraction from *Neopetrosia* sp.

*Neoprotechnic* sp., a marine sponge, were extracted with ethanol (EtOH) and then partitioned with distilled water ($H_2O$) and n-butanol (n-BuOH).

The n-BuOH-soluble material was concentrated in vacuo and partitioned with EtOH and n-hexane.

The EtOH layer was chromatographically separated on a YMC gel column and then purified using reversed-phase high performance liquid chromatography (HPLC) to obtain Neopetroside A (NPS A) and Neopetroside B (NPS B).

The NPS A and NPS B were subjected to NMR analysis. The results are shown below and in Table 1 below.

NPS A: Light yellow, amorphous solid; UV (EtOH)$\lambda_{max}$ (log ε) 260 (3.54); ECD (EtOH, c 2.66×10$^{-4}$ M) $\lambda_{max}$ (Δε) 275 (+0.21) nm; IR (KBr) $v_{max}$ 3417, 1708, 1642, 1608, 1385 cm$^{-1}$; $^1$H, $^{13}$C NMR, Table 1; HRESIMS m/z 376.1033 [M+H]$^+$ (calcd for $C_{18}H_{17}NO_8$, 376.1027) and 398.0854 [M+Na]$^+$ (calcd for $C_{18}H_{17}NNaO_8$, 398.0846).

NPS B: Light yellow, amorphous solid; UV (EtOH) $\lambda_{max}$ (log ε) 266 (3.33); ECD (EtOH c 2.04×10$^{-4}$ M) $\lambda_{max}$ (Δε) 275 (+0.18) nm; $^1$H, $^{13}$C NMR (CD$_3$OD), Table 1; $^1$H NMR (500 MHz, DMSO-d$_6$) δH 11.97 (1H, s, H–1), 9.14 (1H, s, H–2), 8.80 (1H, m, H–4), 8.02 (1H, m, H–5), 8.89 (1H, m, H–6), 6.56 (1H, d, J=5.3 Hz, H–1'), 4.63 (1H, m, H–2'), 4.23 (1H, dd, J=3.4, 4.5 Hz, H–3'), 4.77 (1H, m, H–4'), 4.38 (1H, dd, J=4.6, 12.2 Hz, H–5') 4.49 (1H, dd, J=3.6, 12.2 Hz, H–5'), 6.89 (1H, dd, J=1.7, 3.7 Hz, H–3"), 6.21 (1H, dd, J=2.5, 3.7 Hz, H–4"), 7.08 (1H, dd, J=1.7, 2.5 Hz, H–5"); HRESIMS m/z 347.0887 [M–H]– (calcd for $C_{16}H_{16}N_2O_7$, 347.0885); HRESIMS/MS m/z 110.0243 [$C_5H_4NO_2$]– (calcd for $C_5H_4NO_2$, 110.0248).

TABLE 1

| | NPS A | | NPS B | |
|---|---|---|---|---|
| position | δC, b type | δH mult (J in Hz) | δC, b type | δH mult (J in Hz) |
| 2 | 144.3, CH | 9.28, s | 144.3, CH | 9.27, s |
| 3 | 139.5, C | | 139.0, C | |
| 4 | 147.9, CH | 8.94, dd (8.0, 1.4) | 148.0, CH | 8.94, m |
| 5 | 127.8, CH | 8.06, dd (8.0, 6.2) | 127.8, CH | 8.06, m |
| 6 | 143.7, CH | 8.96, dd (6.2, 1.4) | 143.7, CH | 8.95, m |
| 7 | 167.2, C | | 168.0, C | |
| 1' | 98.6, CH | 6.50, d (5.3) | 98.7, CH | 6.48, d (5.3) |
| 2' | 74.4, CH | 4.79, m | 74.4, CH | 4.81, m |

TABLE 1-continued

| | NPS A | | NPS B | |
|---|---|---|---|---|
| position | δC, b type | δH mult (J in Hz) | δC, b type | δH mult (J in Hz) |
| 3' | 73.3, CH | 4.33, dd (3.8, 4.5) | 73.3, CH | 4.33, dd (3.4, 4.5) |
| 4' | 88.0, CH | 4.96, ddd (3.8, 3.6, 4.6) | 88.2, CH | 4.93, ddd (3.4, 3.6, 4.6) |
| 5' | 65.3, CH$_2$ | 4.50, dd(4.6,12.2) 4.59, dd (3.6, 12.2) | 64.7, CH$_2$ | 4.48, dd(4.6, 12.2) 4.57, dd (3.6, 12.2) |
| 1" | 122.3, C | | | |
| 2" | 133.6, CH | 7.93, d (8.8) | 123.6, C | |
| 3" | 117.0, CH | 6.86, d (8.8) | 117.7, CH | 6.95, dd (1.7, 3.7) |
| 4" | 164.5, C | | 111.6, CH | 6.21, dd (2.5, 3.7) |
| 5" | 117.0, CH | 6.86, d (8.8) | 125.9, CH | 7.01, dd (1.7, 2.5) |
| 6" | 133.6, CH | 7.93, d (8.8) | 163.4, C | |
| 7" | 168.2, C | | | |

[a]Spectra were recorded at 500 MHz for $^1$H NMR and 125 MHz for $^{13}$C NMR.
[b]$^{13}$C NMR assignments were supported by HSQC and HMBC data.

2. NPS A synthesis

Or NPS A can be synthesized as shown in the following Reaction Scheme 1 using a new acetonide defense.

1. Step 1

P-acetoxybenzoyl chloride (313 mg, 1.6 mmol, 1.2 eq.) was added to the agitated pyridine solution (3 ml) containing riboside 9 (240 mg, 1.33 mmol).

The mixture was stirred at room temperature for 30 minutes, then diluted with dichloromethane, washed with 1M HCl and water and saturated with an equal volume of NaHCO$_3$ solution. Thereafter, it was dried and concentrated in vacuo.

The residue was subjected to silica gel column chromatography on a 1:3 volume ratio of ethyl acetate-toluene. As a result, 421 mg (90%) of a riboside 10 compound was obtained as a mixture of anomers.

HMRS-ES positive mode: m/z found 375.1059 [M+Na]$^+$; calcd. for C$_{17}$H$_{20}$NaO$_8$ 375.1056.

2. Step 2

A stirred solution of riboside 10 (120 mg, 0.34 mmol) and ethyl nicotinate 5 (154 mg, 1.02 mmol) was added into dichloromethane (1.5 ml) in triflic anhydride (0.154 mL, 0.98 mmol, 2.7 eq., 3.0 eq.) at 0° C.

[Reaction Scheme 1]

8
Neopetroside A

The mixture was stirred at room temperature for 30 minutes, then quenched in methanol and concentrated. gel The residue was triturated with ether and the precipitate was subjected to silica gel column chromatography on silica (dichloromethane→dichloromethane-methanol in a 95:5 volume ratio) to obtain nicotinoyl ribose 11 of 162 mg (72%).

$R_f$ 0.52 (15% MeOH—$CHCl_3$); $[\alpha]D^{22}$ −3° (c 1, MeOH); δH (600 MHz, $CD_3OD$): 0.99 and 1.28 (both s, 6H, $Me_2C$); 1.36 (t, 3H, J=7.1, $COOCH_2CH_3$), 2.33 (s, 3H, Ac); 4.49 (q, 2H, $COOCH_2CH_3$), 4.75 (dd, 1H, J=3.9 and 12.9, H-5'a), 4.87 (br.d, H-5'b), 4.99 (m, 1H, H-4'), 4.70-4.79 (m, 2H, H-2' and H-3'), 6.63 (d, 1H, J=5.2, H-1'), 7.20 and 8.02 (both d, 4H, J=8.5, H-2", H-3", H-5", H-6"), 8.25 (m, 1H, H-5), 9.12 (d, 1H, J=8.0, H-4), 9.36 (d, 1H, J=6.2, H-6), 9.59 (s, 1H, H-2); HMRS-ES positive mode: m/z found 486.1761 [M]+; calcd. for $C_{25}H_{28}NO_9$ 486.1759.

3. Step 3

To 2 ml of stirred acetonitrile containing nicotinoyl riboside 11 (150 mg, 0.236 mmol), 1.4 N aq. ammonia solution of 2.5 ml was added.

The mixture was stirred at room temperature for 4 hours, then diluted with water and concentrated under a dry condition.

The residue was subjected to silica gel column chromatography using [90% MeOH—$H_2O$)=dichloromethane 25→50%] to obtain 72 mg (74%) of nicotinoyl riboside 12.

$R_f$ 0.36 ($CHCl_3$-MeOH—$H_2O$ 10:10:1); HMRS-ES positive mode: m/z found 416.1341 [M+H]+; calcd. for $C_{21}H_{21}NO_8$ 416.1340.

4. Step 4

Nicotinoyl riboside 12 (65 mg, 0.157 mmol) was dissolved in 2 ml of 90% aqueous trifluoroacetic acid (TFA) and the mixture was allowed to stand at room temperature for one hour. After concentrating in vacuo, it was dissolved in water and lyophilized to obtain 74 mg (97%) of nicotinoyl riboside 8 (neopetroside A) in the form of a salt.

$R_f$ 0.36 ($CHCl_3$/MeOH/$H_2O$, 10:10:1); $[\alpha]D$ 19+20 (c 1, $H_2O$); δH (600 MHz, $CD_3OD$): 4.37 (dd, 1H, J=3.8 and 4.6, H-3'), 4.51 (dd, 1H, J=4.5 and 12.3, H-5'a), 4.59 (dd, 1H, J=3.5 and 12.3, H-5'b), 4.80 (m, 1H, H-2'), 4.98 (m, 1H, H-4'), 6.54 (d, 1H, J=5.2, H-1'), 6.86 (d, 2H, J=8.5, H-3", H-5"), 7.93 (d, 2H, J=8.5, H-2", H-6"), 8.17 (dd, 1H, J=6.8 and 7.9, H-5), 9.02 (dd, 1H, J=1.3, 8.0, H-4), 9.12 (dd, 1H, J=1.4 and 6.2, H-6), 9.38 (s, 1H, H-2); HMRS-ES positive mode: m/z found 398.0849 $[M+Na]^+$; calcd. for $C_{18}H_{17}NNaO_8$ 398.0846.

This can reduce the cost of extraction solvents and reagents and achieve the target compound faster than chromatography. Also, it can reduce the required steps without loss of total yield.

In addition, 2,3-acetonide of D-ribose was used as a starting material and a step of conditions for forming N-glycoside bond ($Tf_2O$ in $CH_2Cl_2$ was used in place of $Ph_3P$ in $CCl_4$) was deleted thereby avoiding the use of an intermediate chlorine-containing derivative.

The NPS A is a safe compound that dissolves in water, and dissolves in pyridine and methanol but is not well soluble in other organic solvents.

It can be present in two forms as shown in Chemical Formula 4 or 5, which can be obtained in acid and neutral media: inner salt (betainic form, Chemical Formula 4) and salt form (Chemical Formula 5).

[Chemical Formula 4]

[Chemical Formula 5]

<Example 2> Confirmation of Toxicity for Cells

In h9c2 cells, myocardial cells, the toxicity of NPS A extracted from *Neopetrosia* sp. Of Example 1 was confirmed.

The h9c2 cells were dispensed at $2 \times 10^4$ cells/well in a 96-well tissue culture plate and cultured for 16 hours. Thereafter, various concentrations of NPS A were treated and cultured for additional 24 hours.

After the culture, a quantitative colorimetric assay using MTT(3-(4,5-dimethylthiazol-2-yl)-2,5-diphenyltetrazolium bromide (Sigma-Aldrich, St. Louis, Mo., USA) was performed to confirm the survival rate of the cells.

The degree of reduction of MTT to intracellular formazan was confirmed by measuring the optical density at 570 nm using a microplate reader (Molecular device, Sunnyvale, Calif., USA).

Figure 2:
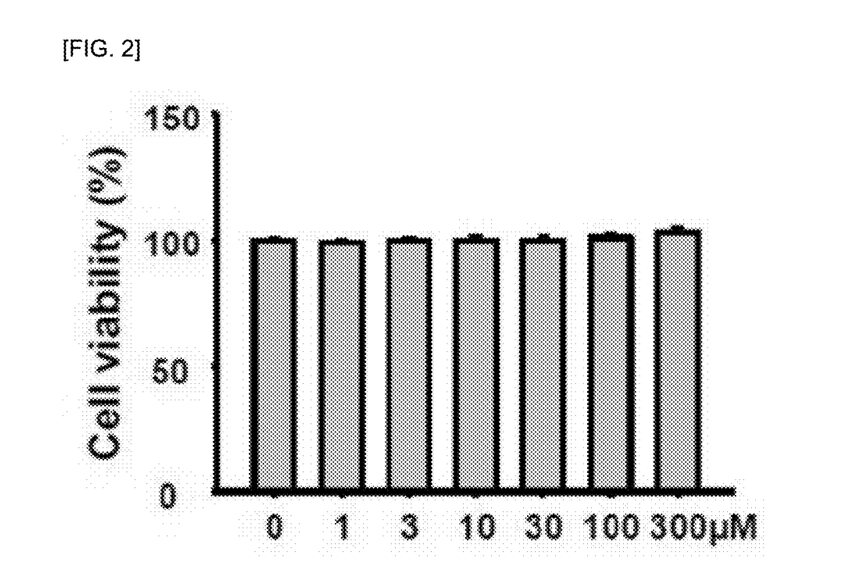
FIG. 2 shows the result of the toxicity of Neoperoside A (NPS A) on myocardial cells.

As a result, as shown in FIG. 2, NPS A was not toxic to the myocardial cells up to a concentration of 300 μM.

Example 3: Confirmation of Activity of NPS a in Myocardial Cells

1. Confirmation of Oxygen Consumption Rate (OCR) and Mitochondrial ATP (Adenosine Triphosphate) Levels In h9c2 cell line, the treatment of NPS A was confirmed that it improved myocardial function and metabolic activity.

For this, the basal oxygen consumption rate (OCR), respiratory related to ATP (adenosine triphosphate), proton leak, maximal capacity and mitochondrial OCR were confirmed.

First, to measure OCR, h9c2 cells were dispensed at $2 \times 10^4$ cells/well in an XF24 cell plate (Seahorse Bioscience, Billerica, Mass., USA) and cultured for 16 hours. Thereafter, cells were dispensed with various concentrations of NPS A and cultured for another one hour. After 1 hour, the medium was replaced with 500 µL of XF assay medium-modified DMEM (XF Assay Medium-modified DMEM, Seahorse Bioscience, Billerica, Mass., USA) and incubated for 1 hour in a incubator at 37° C. in absence of $CO_2$.

OCR was measured using an XF24 analyzer (Seahorse Bioscience, Billerica, Mass., USA) and XF24 software. After OCR measurement, the XF 24 assay results were normalized to the cell number and the number of cells in each well was counted by a Luna™ automated cell counter (Logos, Annandale, Va., USA).

Furthermore, mitochondrial ATP levels were measured using the Mitochondrial T ToxGlo™ assay (Promega, Madison, Wis., USA) according to the manufacturer's instructions.

Briefly, h9c2 cells were dispensed at $2\times10^6$ cells/well in a 60 mm tissue culture plate and cultured for 16 hours and treated with 0, 3, or 10 µM NPS A for 1 hour. The treated cells were all collected and resuspended by pipetting until the cells were uniformly dispersed. The resuspended h9c2 cells were dispensed at $2\times10^4$ cells/well in a 96-well plate and the plates were centrifuged at 200×g for 10 minutes to remove the medium. Thereafter, 50 µL of fresh medium (except for glucose, containing 10 mM galactose) was added.

The cells were incubated in a humidified incubator at 37° C. supplied with $CO_2$ for 90 minutes. Then, the assay solution (100 µL) was added to the plate and reacted at room temperature for 30 minutes. Luminescence was measured using a luminometer (Molecular Device, Sunnyvale, Calif., USA).

Figure 3:
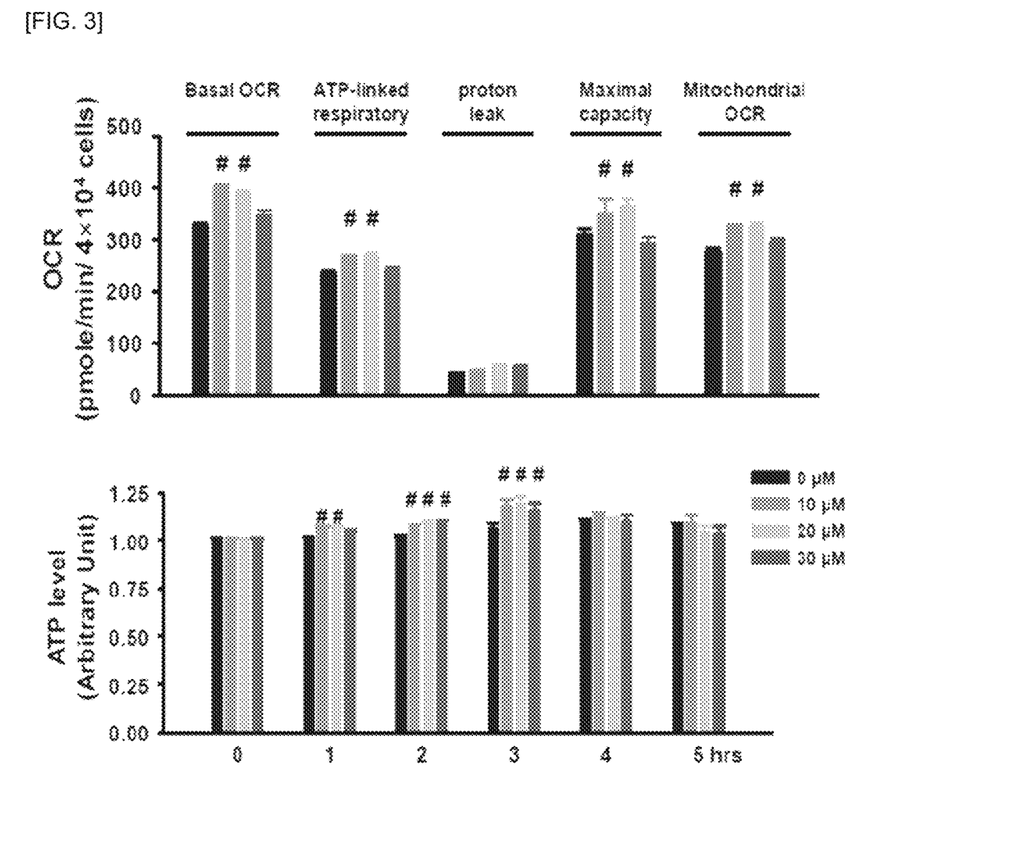
FIG. 3 shows the results of the oxygen consumption rate (OCR) and the mitochondrial ATP (adenosine triphosphate) level after treating myocardial cells with NPS A at various concentrations.

As a result, as shown in FIG. 3, NPS A stimulates ATP synthesis and increases intracellular ATP levels in the same cells.

In other words, NPS A up-regulated oxidative phosphorylation, basal and mitochondrial OCR, respiration associated with ATP and ATP synthesis in myocardial cells.

Figure 4:
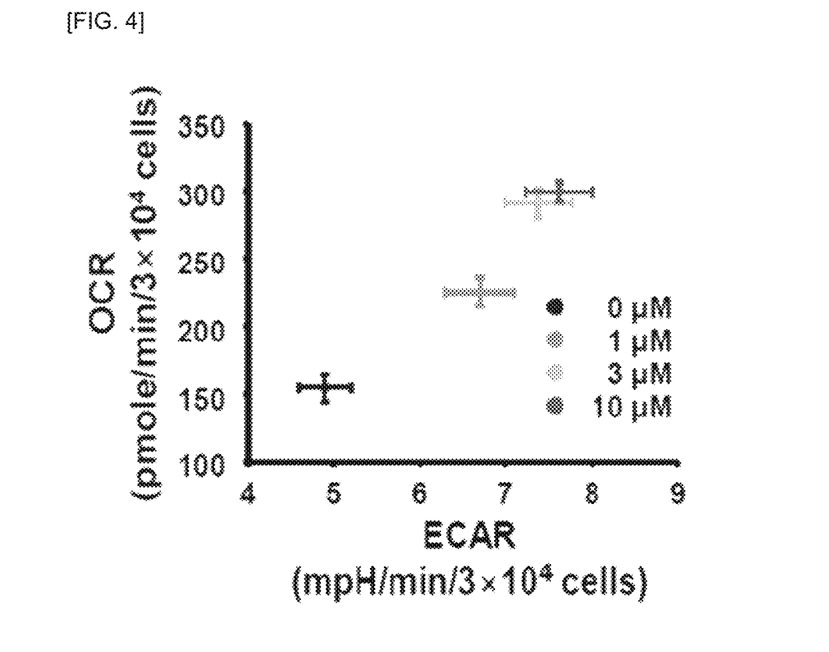
FIG. 4 shows the result of the ratio of OCR/extracellular acidification rate (ECAR) according to NPS concentration.

On the other hand, as shown in FIG. 4, NPS A increased not only the basal ECAR (extracellular acidification rate) and the basal OCR, but also the OCR/ECAR ratio.

2. Confirmation of Effect on Glycolysis

After treating h9c2 cells with NPS A, the glycolysis activity, the glycolysis capacity and the glycolysis reserve were confirmed using an XF24 analyzer.

h9c2 cells were treated sequentially with 10 mM glucose (G), 1 µM oligomycin (O) and 10 mM 2-dioxyglucose (2DG), treated with NPS A for 1 hour and then measured with an XF24 analyzer.

Figure 5:
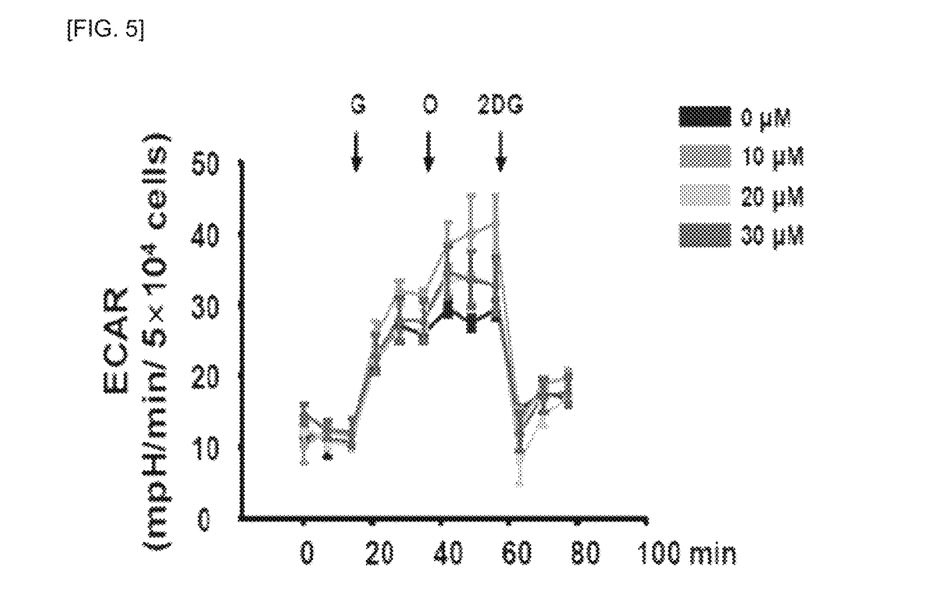
FIG. 5 shows the result of confirming the glycolysis after treating NPS A at various concentrations.

As a result, as shown in FIG. 5, when the h9c2 cells were treated with 10 µM of NPS A compared to the high concentration treatment (20 µM or 30 µM), they exhibited the greatest glycolysis activity and glycolysis capacity.

Therefore, it is confirmed that NPS A affected energy metabolism and enhanced the glycolysis activity and oxidative posphorylation and increased the level of ATP synthesis.

<Example 4> Confirmation of Neoprotease a (NPS A) Activity in Ischemic Reperfusion Heart Model 1. Ischemic Reperfusion Injury Modeling 8-week-old male SD rats (200-250 g) were anesthetized by intraperitoneal injection of sodium pentobarbital (100 mg/kg). The chest cavity was exposed and a glass cannula was inserted into the aorta. The heart was quickly cut into thoracotomy, perfused with a normal Tyrode's solution in a Langendorff system and equilibrated with 95% $O_2$ and 5% $CO_2$ at 37° C. for 10 min to remove all blood.

2. NPS a Treatment and Ventricular Pressure Recovery Effect Confirmation

The heart of the rat was extirpated and the experiment was performed using a non-circulating system.

First, ischemic reperfusion (I/R) model and drug treatment group (NPS A treatment; NPS A 10 µM treatment after ischemia reperfusion) were performed and hypoxic solution was flowed for 30 minutes. After 30 minutes, the normal tyrode solution and NPS A were treated together to restore cardiac function and confirm changes in electrocardiogram.

Figure 6:
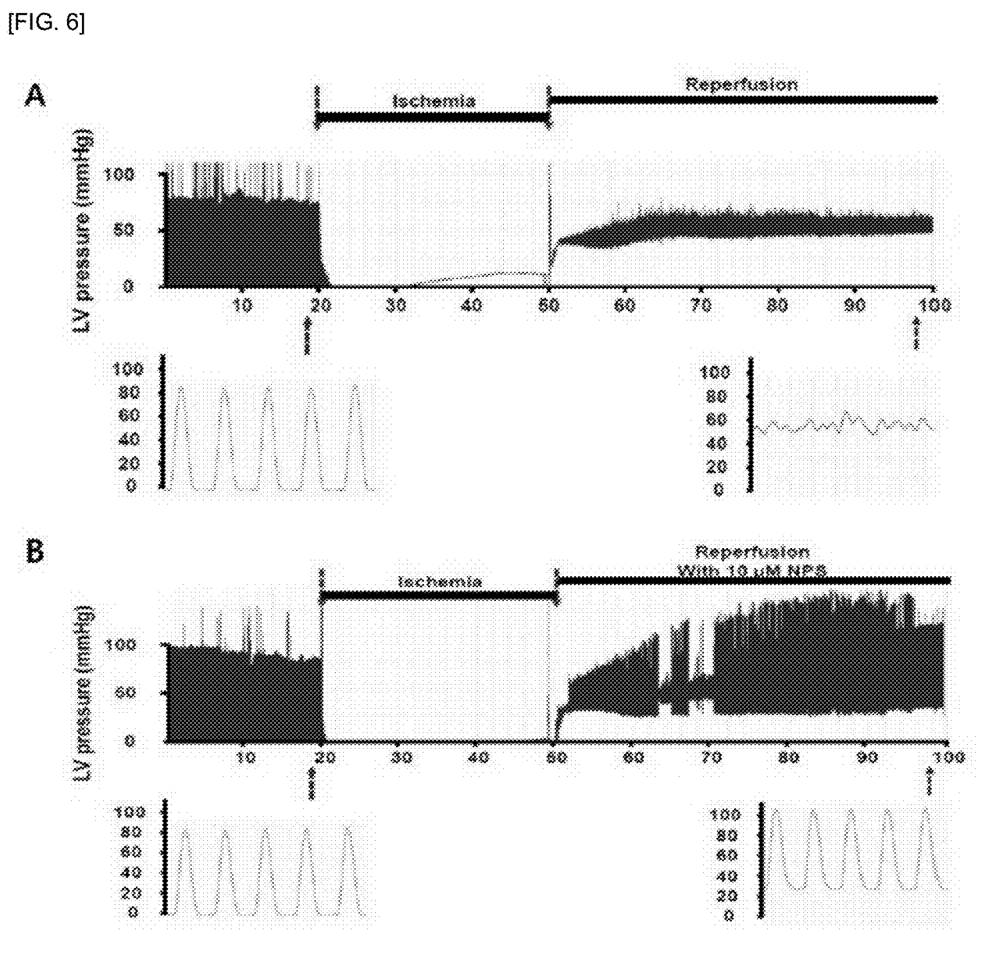
FIG. 6 shows the result of confirming the activity of NPS A in the ischemic reperfusion heart model.

As a result, as shown in FIGS. 6A and 6B, the heart was blocked to induce global ischemia (30 minutes) followed by reperfusion (50 minutes). After global ischemia (initiating reperfusion), 10 µM of NPS A was administered for 30 minutes.

As shown in FIG. 6A, left ventricular pressure (LV pressure) due to ischemic reperfusion was not recovered in the ischemic reperfusion experimental group, but left ventricular pressure was effectively restored in the group treated with NPS A at the same time during the reperfusion as shown in FIG. 6B.

In addition, the cardiac rhythm was recovered and the size of the heart infarction was significantly reduced.

3. Confirmation of Effect of Oxidative Phosphorylation in Mitochondria Extracted from NPS A-Treated Rat Heart OCR was significantly reduced during the three stages of mitochondrial respiration in the mitochondria extracted from cardioblasts of I/R rat group, but the fourth stage of respiration did not change in mitochondria of any group On the other hand, treatment with NPS A significantly protected the three-stage respiratory depression in mitochondria.

Figure 7:
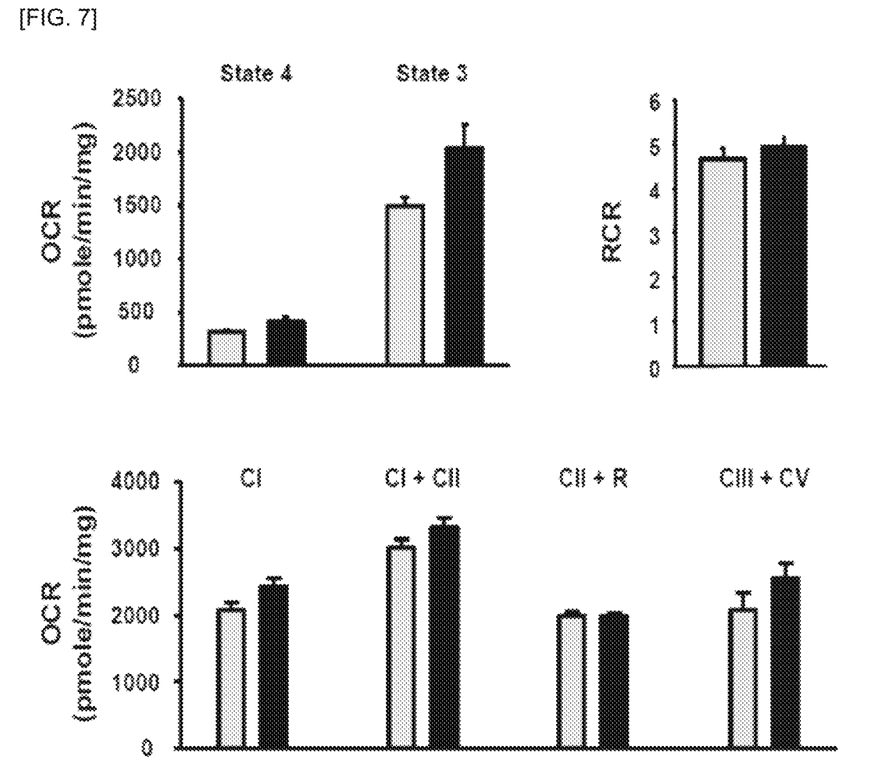
FIG. 7 shows the results of confirming the effect of oxidative phosphorylation in mitochondria extracted from the heart of rats treated with NPS A.

Therefore, as shown in FIG. 7, the respiratory control ratio (RCP) was recovered by the NPS A treatment.

<Example 5> Confirmation of NPS a Activity in Ischemic Reperfusion Myocardial Cells During NPS A administration, it was confirmed whether it affected the kinase associated with cell survival.

First, kinases regulated by NPS A were screened using a set of kinases related to cardiovascular diseases and diabetes.

Figure 8:
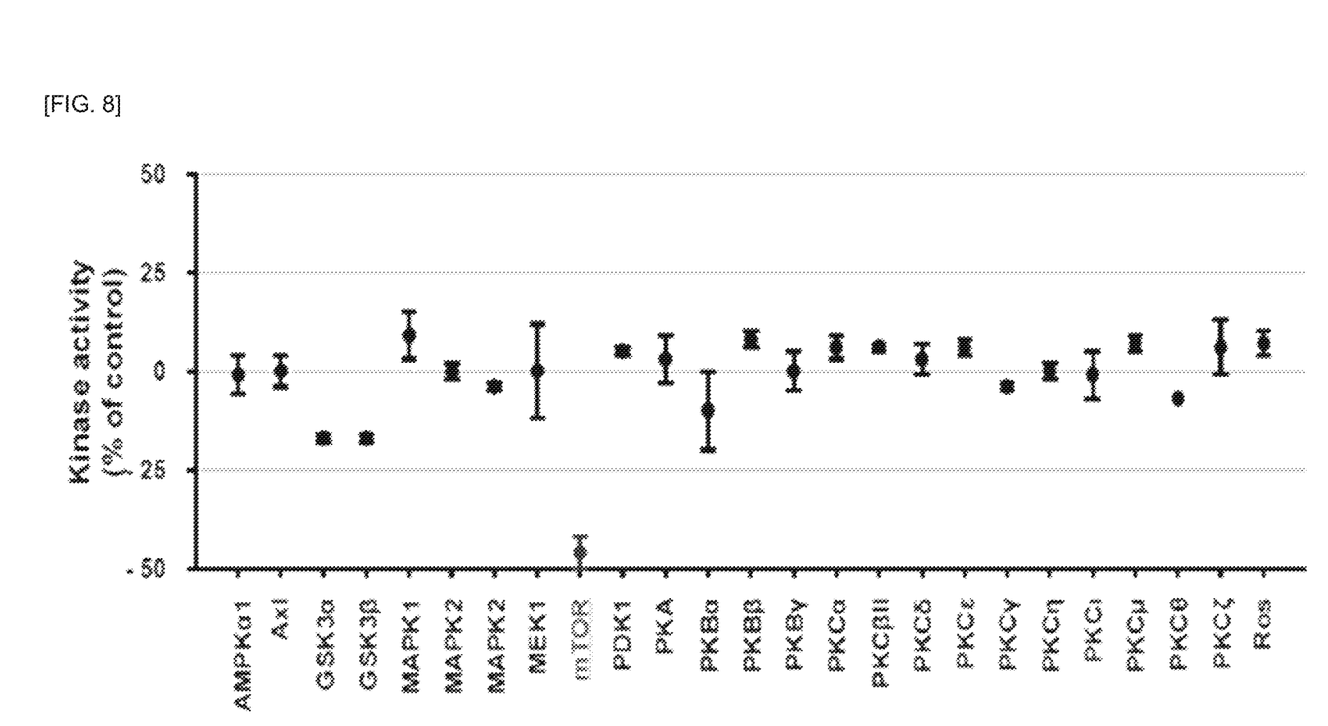
FIG. 8 shows the results of screening of kinases regulated by NPS A using kinase set associated with cardiovascular diseases and diabetes.

As a result, as shown in FIG. 8, it was found that NPS A did not regulate most of the candidate kinases of the first type.

On the other hand, it was confirmed that GSK-3α (Glycogen synthase kinase-3α), GSK-3β and mTOR (mammalian target of rapamycin) among kinases related with diabetes were inhibited.

The activity of GSK-3 alpha, GSK-3 beta and mTOR kinase regulated by NPS A was measured to determine the half maximal inhibition dosage.

The $IC_{50}$ of NPS A was 140 µM for GSK-3α and 124 µM for GSK-3β. On the other hand, no change in mTOR activity according to another doses of NPS A was observed.

While this invention has been described in connection with what is presently considered to be practical exemplary embodiments, it is to be understood that the invention is not limited to the disclosed embodiments, but, on the contrary, is intended to cover various modifications and equivalent arrangements included within the spirit and scope of the appended claims.

The invention claimed is:

1. A method of preparing a pyridine nucleoside compound represented by Neopetroside A or a pharmaceutically acceptable salt thereof, as following Reaction Scheme 1, comprising:
- preparing riboside compound of Compound 10 by adding p-acetoxybenzoyl chloride to riboside solution of Compound 9;
- preparing nicotinoyl riboside compound of Compound 11 by adding ethyl nicotinate to riboside solution of the Compound 10;
- preparing a nicotinoyl riboside compound of Compound 12 by adding an ammonium solution to nicotinoyl ribose solution of the Compound 11; and
- preparing a neopetroside compound of Compound 8 by dissolving nicotinoyl ribose of the Compound 12 in an aqueous solution of trifluoroacetic acid, and concentrating and lyophilizing,

[Reaction Scheme 1]

Neopetroside A

2. A method of preventing or treating ischemic heart disease in a subject in need thereof, comprising:
providing a pharmaceutical composition comprising a pyridine nucleoside compound represented by following Chemical Formula 1 or a pharmaceutically acceptable salt thereof, as an active ingredient:

[Chemical Formula 1]

in Chemical Formula 1, $R^1$ is a heteroaromatic group or phenol; and
administering the pharmaceutical composition to the subject, wherein the ischemic heart disease is prevented or treated.

3. The method of claim 2, wherein the pyridine nucleoside is a compound represented by following Chemical Formula 2 or Chemical Formula 3:

[Chemical Formula 2]

[Chemical Formula 3]

4. The method of claim 2, wherein the ischemic heart disease is any one selected from the group consisting of myocardial infarction, heart failure and angina pectoris.

* * * * *